(12) United States Patent
Jeong et al.

(10) Patent No.: US 9,943,534 B2
(45) Date of Patent: Apr. 17, 2018

(54) COMPOSITION FOR PREVENTING OR TREATING LIVER CANCER CONTAINING GINSENOSIDE F2

(71) Applicant: INTELLIGENT SYNTHETIC BIOLOGY CENTER, Daejeon (KR)

(72) Inventors: Won Il Jeong, Daejeon (KR); Myung Ho Kim, Daejeon (KR); Jong Min Jeong, Daejeon (KR); So Yeon Kim, Daejeon (KR); Sun Chang Kim, Daejeon (KR)

(73) Assignee: INTELLIGENT SYNTHETIC BIOLOGY CENTER, Daejeon (KR)

( * ) Notice: Subject to any disclaimer, the term of this patent is extended or adjusted under 35 U.S.C. 154(b) by 0 days.

(21) Appl. No.: 15/461,739

(22) Filed: Mar. 17, 2017

(65) Prior Publication Data

US 2018/0036324 A1 Feb. 8, 2018

(30) Foreign Application Priority Data

Aug. 5, 2016 (KR) .................. 10-2016-0099978

(51) Int. Cl.
*A61K 31/704* (2006.01)
(52) U.S. Cl.
CPC .................. *A61K 31/704* (2013.01)
(58) Field of Classification Search
None
See application file for complete search history.

(56) References Cited

FOREIGN PATENT DOCUMENTS

| EP | 2992933 | 3/2016 |
|---|---|---|
| KR | 10-2012-0057125 | 6/2012 |
| KR | 10-1360231 | 4/2013 |
| KR | 10-1433661 | 12/2013 |
| KR | 10-2016-0029894 | 3/2016 |
| WO | WO 2009/125964 | 10/2009 |
| WO | WO 2016/190481 | 12/2016 |

OTHER PUBLICATIONS

Wu et al., "Anticarcinogenic Effect of red Ginseng on the Development of Liver Cancer Induced by Diethylnitrosamine in Rats", Journal of Korean Medical Sciences, 2001, vol. 16(suppl), pp. S61-S65.*
Ginsenoside F2 product details, APExBIO, printed from web Jul. 10, 2017.*
Hwang, In Guk, et al. "Chances in ginsenosides and antioxidant activity of Korean ginseng (Panax ginseng CA Meyer) with heating temperature and pressure." Food Science and Biotechnology 19.4 (2010): 941-949.
Kim, Sung Gi, et al. "Microwave Heating Rapidly Alters Ginsenoside Composition of Fresh Ginseng (Panax ginseng CA Meyer)." Journal of Food and Nutrition Research 4.6 (2016): 394-399.
Lee, So Jim, Yunjeong Kim, and Min-Gul Kim. "Changes in the ginsenoside content during the fermentation process using microbial strains." Journal of ginseng research 39.4 (2015): 392-397.
Xiao, Dan, et al. "A comparative study on chemical composition of total saponins extracted from fermented and white ginseng under the effect of macrophage phagocytotic function." Journal of Ginseng Research.
European Search Report issued in European Application No. 17161693, dated May 23, 2017.
Ji et al., "Determination of ginsenosides by *Bacillus polymyxa* conversion and evaluation on pharmacological activities of the conversion products", Process Biochemistry, 50(6): 1016-1022, 2015.
Chen, X-J., et al., "Anticancer Activities of Protopanaxadiol- and Protopanaxatriol-Type Ginsenosides and Their Metabolites", Evidence-Based Complementary and Alternative Medicine, vol. 2016, Article ID 5738694, 19 pages. Epub Jun. 30, 2016.
Cheong, J.H., et al., "Stereoisomer-Specific Anticancer Activities of Ginsenoside Rg3 and Rh2 in HepG2 Cells: Disparity in Cytotoxicity and Autophagy-Inducing Effects Due to 20(S)-Epimers", Biol. Pharm. Bull., 2015, vol. 38, pp. 102-108.
Jiang, J-W., et al., "Ginsenoside Rg3 inhibit hepatocellular carcinoma growth via intrinsic apoptotic pathway", World Journal of Gastroenterology, 2011, vol. 17(31), pp. 3605-3613.
Lee, J-Y., et al., "Sensitization of Trail-Induced Cell Death by 20(S)-Ginsenoside Rg3 via CHOP-Mediated DR5 Upregulation in Human Hepatocellular Carcinoma Cells", Molecular Chemical Therapeutics, 2013, vol. 12(3), pp. 274-285.
Mai, T.T., et al., "Ginsenoside F2 induces apoptosis accompanied by protective autophagy in breast cancer stem cells", Cancer Letters, 2012, vol. 321, pp. 144-153.
Mao, Q., et al., "Chemical profiles and anticancer effects of saponin fractions of different polarity from the leaves of Panax notoginseng", Chinese Journal of Natural Medicines, 2014, vol. 12(1), pp. 30-37.
Mao, Q., et al., "Ginsenoside F2 induces apoptosis in humor gastric carcinoma cells through reactive oxygen species-mitochondria pathway and modulation of ASK-1/JNK signaling cascade in vitro and in vivo", Phytomedicine, 2014, vol. 21, pp. 515-522.
Shin et al., "Anti-cancer effect of Ginsenoside F2 against glioblastoma multiforme in xenograft model in SD rats", J. Ginseng Res., Jan. 2012, vol. 36, No. 1, pp. 86-92.
Toh, D-F., et al., "Anti-proliferative effects of raw and steamed extracts of Panax notoginseng and its ginsenoside constituents on human liver cancer cells", Chinese Medicine, 2011, 6:4 | http://www.cmjournal.org/content/6/1/4.
Yang, Z., et al., "Ginsenoside Rh2 inhibits hepatocellular carcinoma through β-catenin and autophagy", Scientific Reports, 6:19383 | DOI: 10.1038/srep19383 Epub Jan. 19, 2016.

(Continued)

Primary Examiner — Traviss C McIntosh, III
(74) Attorney, Agent, or Firm — Parker Highlander PLLC (57) ABSTRACT

The present invention relates to a composition for preventing or treating liver cancer containing ginsenoside F2 as an active ingredient. Specifically, the composition according to the present invention kills liver cancer cells, specifically inhibits the formation of liver cancer, and reduces the expression of alanine aminotransferase (ALT) or aspartate aminotransferase (AST), without affecting normal hepatocytes, and thus can be usefully used as a therapeutic agent for liver cancer.

6 Claims, 12 Drawing Sheets

(56) References Cited

OTHER PUBLICATIONS

Zheng, Y., et al., "Antiproliferative effects of protopanaxadiol ginsenosides on human colorectal cancer cells", Biomedical Reports, 2013, vol. 1, pp. 555-558.
Zheng, Z-Z., et al., "Compound K-induced apoptosis of human hepatocellular carcinoma MHCC97-H cells in vitro", Oncology Reports, 2014, vol. 32, pp. 325-331.
Zhu, G-Y., et al., "20(S)-Protopanaxadiol, a metabolite of ginsenosides, induced cell apoptosis through endoplasmic reticulum stress in human hepatocarcinoma HepG2 cells", European Journal of Pharmacology, 2011, vol. 668, pp. 88-98.

* cited by examiner

COMPOSITION FOR PREVENTING OR TREATING LIVER CANCER CONTAINING GINSENOSIDE F2

This application claims the benefit of Korean Patent Application No 10-2016-0099978, filed Aug. 5, 2016, the entirety of which is incorporated herein by reference.

TECHNICAL FIELD

The present invention relates to a pharmaceutical composition for preventing or treating liver cancer containing ginsenoside F2 as an active ingredient.

Further, the present invention relates to a health functional food composition for preventing or improving liver cancer containing ginsenoside F2 as an active ingredient.

Furthermore, the present invention relates to a method for preventing or treating liver cancer, comprising administering a composition containing ginsenoside F2 to a subject.

BACKGROUND ART

The liver cancer which occurs in 74.8 males and 15.6 females based on 100,000 Korean middle-aged men and women (40-60 years old) is a disease with the highest mortality rate leading to 24.1 deaths in 100,000 people per year (according to the data from National Cancer Information Center, Korea in 2013).

Currently, the best way to treat liver cancer is by means of surgical resection and liver transplantation. However, in the case of liver transplantation, it is difficult to find donors, whereas in the case of surgical resection, the number of patients on whom the surgery can be performed is limited to within 20% of all patients. Thus, they are not suitable as a method for treating all patients with liver cancer.

Other treatment methods include systemic chemotherapy, hepatic artery chemoembolization, hepatic artery chemotherapy infusion, and radiotherapy, etc., but these treatments not only kill liver cancer cells but also normal cells, giving rise to a fatal side effect.

In addition, it has been reported that Nexavar, which is the world's first oral therapeutic agent typically used for the treatment of liver cancer and which contains the ingredients of sorafenib, has caused side effects such as reduced pancreas when taken over a long period of time. Therefore, studies on liver cancer therapeutic agents without causing side effects have been actively conducted.

On the other hand, ginsenosides are a class of saponin in ginseng, and there exist more than 30 kinds of ginsenosides. According to their structures, they are classified as PPD (protopanaxadiol) and PPT (protopanaxatriol), and they are known to exhibit different pharmacological activities depending on their chemical structures (*Curr Vasc Pharmacol.* 2009 July; 7(3):293-302). Among the ginsenosides, the minor ginsenosides which are present in a very small amount in ginseng are difficult to isolate, and thus their research is insufficient.

Accordingly, the present inventors have made extensive effort to find a composition which exhibits an excellent therapeutic effect on liver cancer, and as a result, they confirmed that ginsenoside F2 can inhibit the formation and proliferation of liver cancer without affecting the normal cells, thereby completing the present invention.

PRIOR ART DOCUMENTS

Patent Documents (Patent Document 1) KR 10-1360231 B1 (Patent Document 2) KR 10-1433661 B1

DISCLOSURE

Technical Problem

One object of the present invention is to provide a pharmaceutical composition for preventing or treating liver cancer containing ginsenoside F2 as an active ingredient.

Another object of the present invention is to provide a health functional food composition for preventing or improving liver cancer containing ginsenoside F2 as an active ingredient.

Still another object of the present invention is to provide a method for preventing or treating liver cancer, comprising administering a composition containing ginsenoside F2 to a subject.

Technical Solution

During the study related to liver cancer therapeutic agents, when the present inventors treated the ginsenoside F2 to mice in which liver cancer was induced, they confirmed that the formation of liver cancer was inhibited and the expression of ALT and AST, which imply the damage of hepatocytes, was reduced without affecting the normal cells, thereby discovering for the first time that the composition containing ginsenoside F2 exhibited an excellent therapeutic effect on liver cancer.

To achieve the objects above, in one aspect of the present invention, there is provided a pharmaceutical composition for preventing or treating liver cancer containing ginsenoside F2 as an active ingredient.

As used herein, the term "ginsenoside F2" is a class of saponin which is the main active ingredient of ginseng or red ginseng, etc. and refers to a ginsenoside belonging to the PPD (protopanaxadiol) group.

The ginsenoside F2 may be obtained by purchasing commercially available products or isolating from ginseng cultivated or harvested in the natural environment, or converting from the isolated ginsenoside to be used. In addition, the ginsenoside F2 synthesized by a synthesis method may be used, but any ginsenoside F2 may be used, without limitations, as long as they are effective in preventing or treating liver cancer.

In one embodiment of the present invention, after separating crude saponin from ginseng, the ginsenoside F2 was prepared from ginsenosides obtained from the crude saponin.

As used herein, the term "prevention" may refer to any action by which the onset of liver cancer is inhibited or delayed by administration of the ginsenoside F2 according to the present invention to a subject.

As used herein, the term "treatment" may refer to any action by which the symptoms of liver cancer have taken a turn for the better or become advantageous by administration of the composition of the present invention to an individual suspected of having the onset of liver cancer.

Figure 4A:
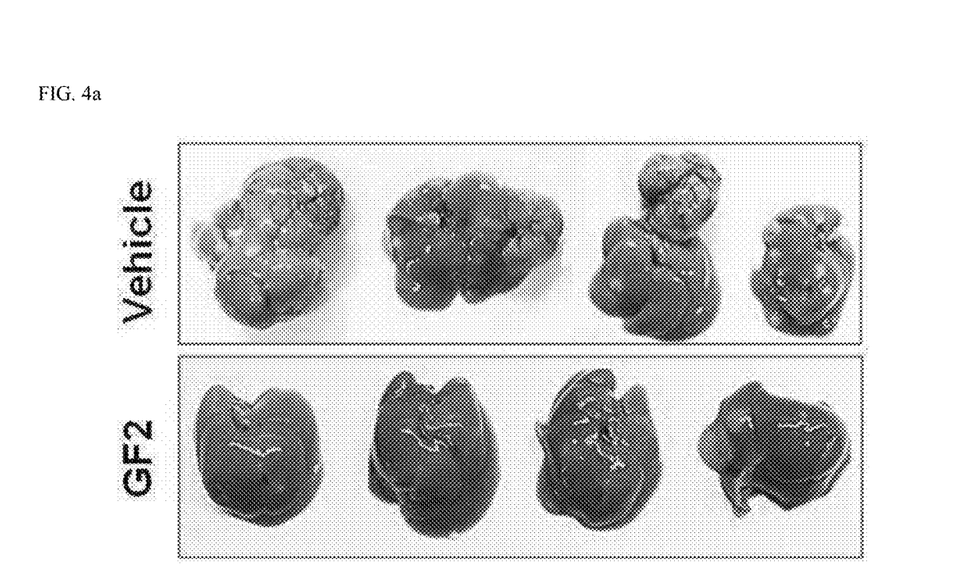
FIG. 4a is an image showing the tumor size formed upon administration of ginsenoside F2 or vehicle to liver cancer-induced mice.
Figure 4B:
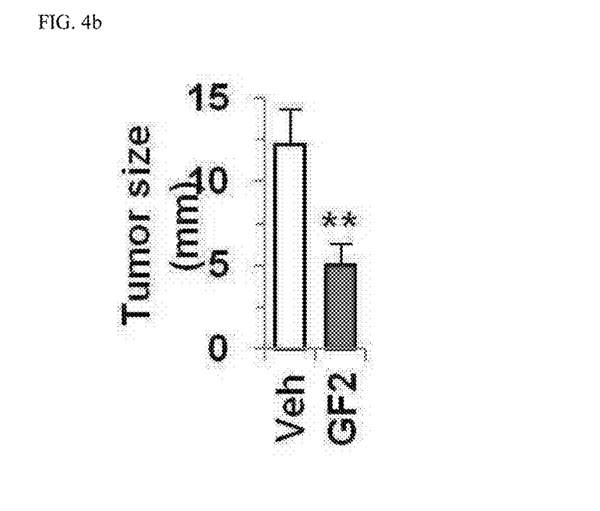
FIG. 4b is an image showing the tumor size formed upon administration of ginsenoside F2 or vehicle to liver cancer-induced mice.
Figure 4C:
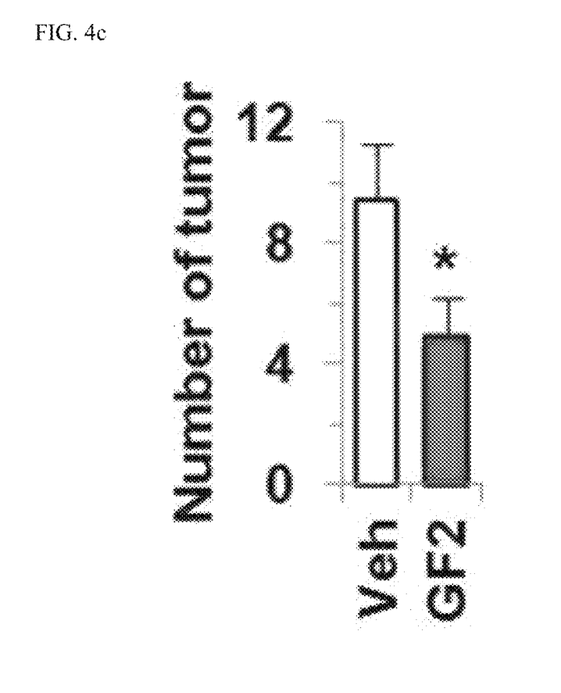
FIG. 4c is an image showing the number of tumor formed upon administration of ginsenoside F2 or vehicle to liver cancer-induced mice.
Figure 4D:
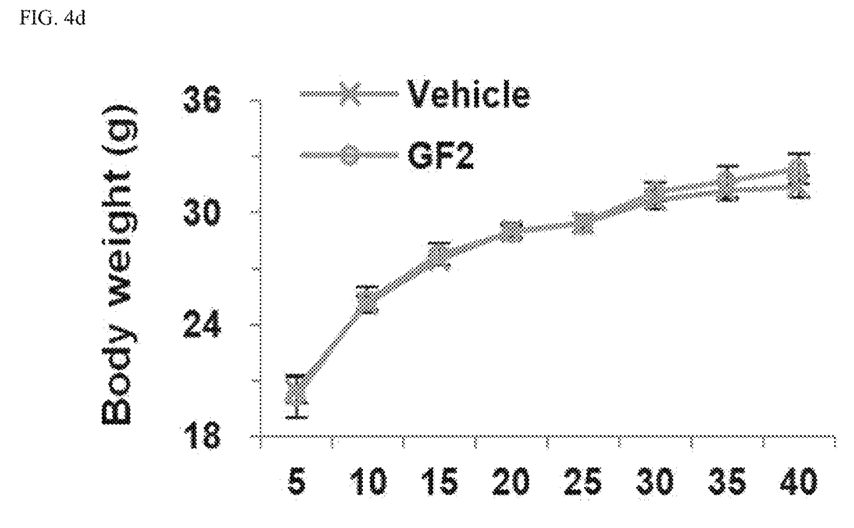
FIG. 4d is an image showing the body weight of mice upon administration of ginsenoside F2 or vehicle to liver cancer-induced mice.
Figure 4E:
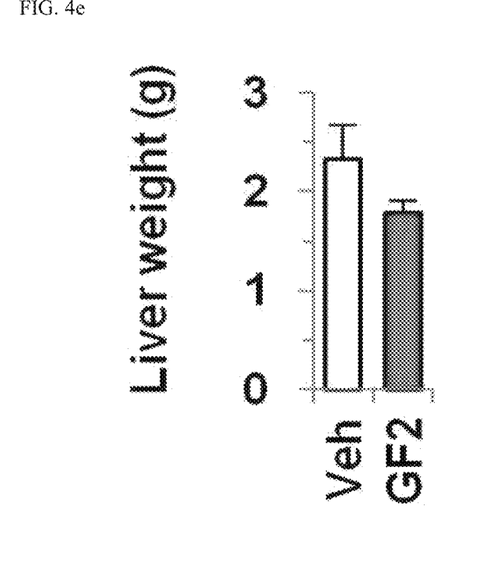
FIG. 4e is an image showing the tumor weight upon administration of ginsenoside F2 or vehicle to liver cancer-induced mice.
Figure 4F:
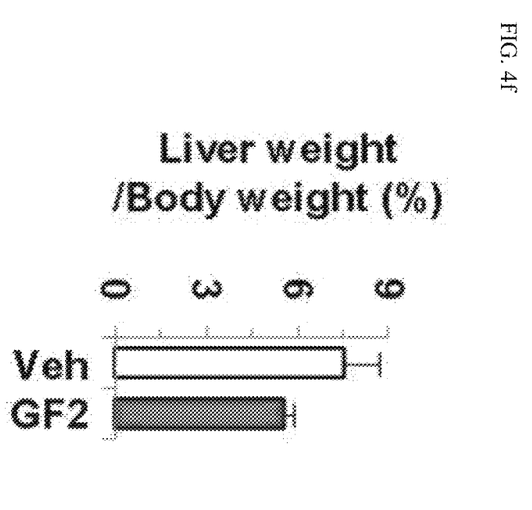
FIG. 4f is an image showing the tumor weight relative to the total weight upon administration of ginsenoside F2 or vehicle to liver cancer-induced mice.

In one embodiment of the present invention, after treating the ginsenoside F2 to mice in which liver cancer was induced, the size, number, and weight of liver cancer tissues were analyzed, and as a result, it was confirmed that the size of the cancer tissues was significantly reduced compared to a vesicle-treated group, and that the number of the cancer tissues was reduced by more than twice (FIGS. 4a to 4c). Further, there was no difference in body weight of both treatment groups, but the weight of the liver tissues was reduced in the ginsenoside F2-treated group compared to the vesicle-treated group (FIGS. 4d to 4f).

Therefore, it was found that the pharmaceutical composition can be effectively used as a preventive or therapeutic agent for liver cancer.

In the present invention, the pharmaceutical composition may exhibit a specific cell-killing effect on liver cancer cells, and the liver cancer cell may be Hep3B, a human liver cancer cell line, or Hepa1-6, a mouse liver cancer cell line, but is not limited thereto, and may generally exhibit a cell-killing effect on all liver cancer cells.

Figure 1A:
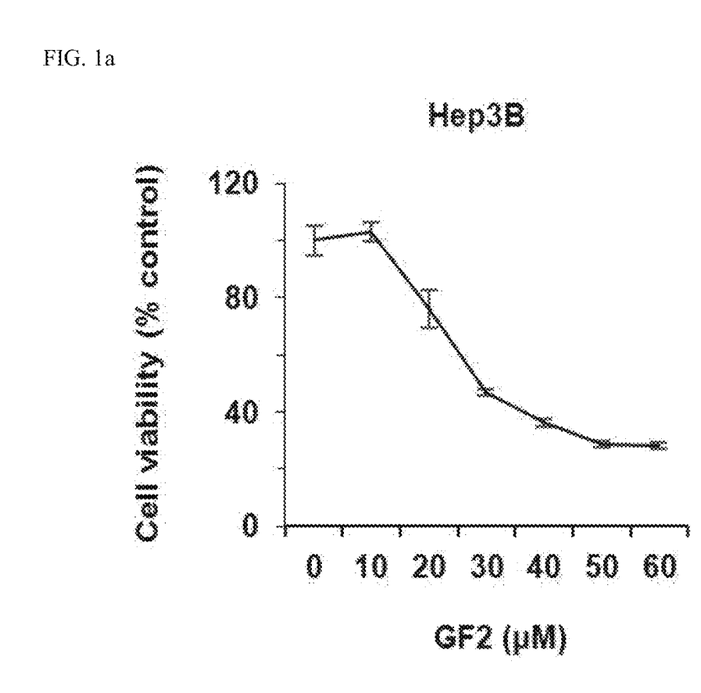
FIG. 1a is a graph showing the cell-killing effect of ginsenoside F2 on human liver cancer cell line (Hep3B).
Figure 1B:
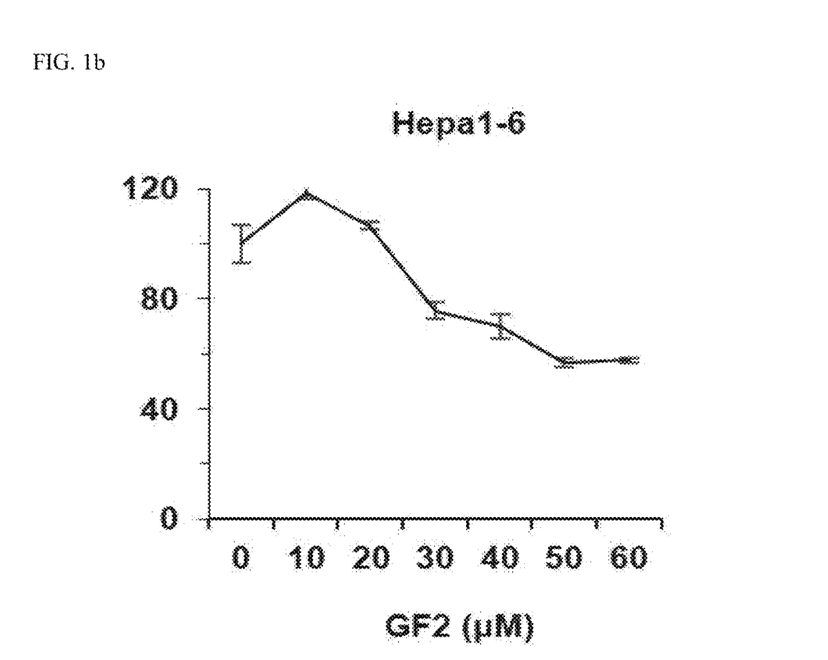
FIG. 1b is a graph showing the cell-killing effect of ginsenoside F2 on mouse liver cancer cell line (Hepa1-6).
Figure 1C:
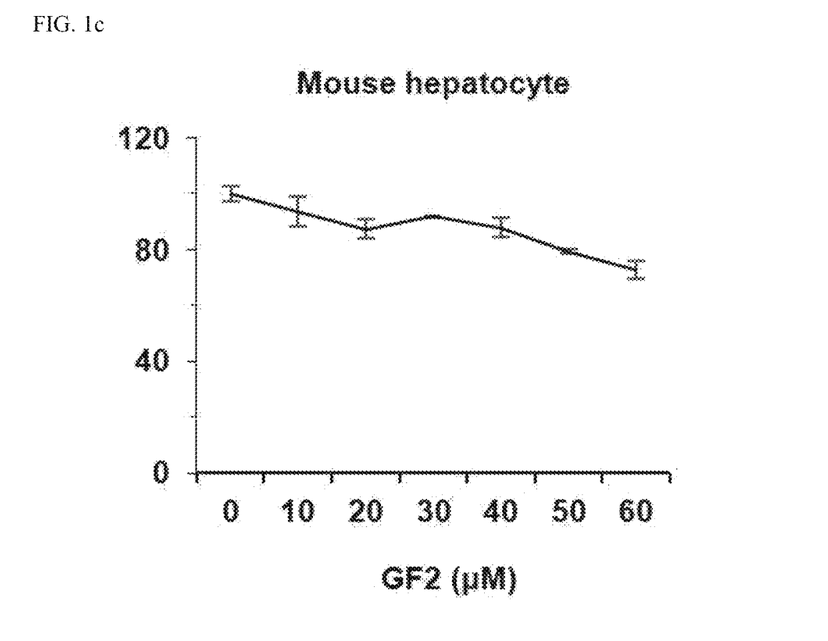
FIG. 1c is a graph showing that ginsenoside F2 does not affect the survival of normal mouse hepatocytes.
Figure 2A:
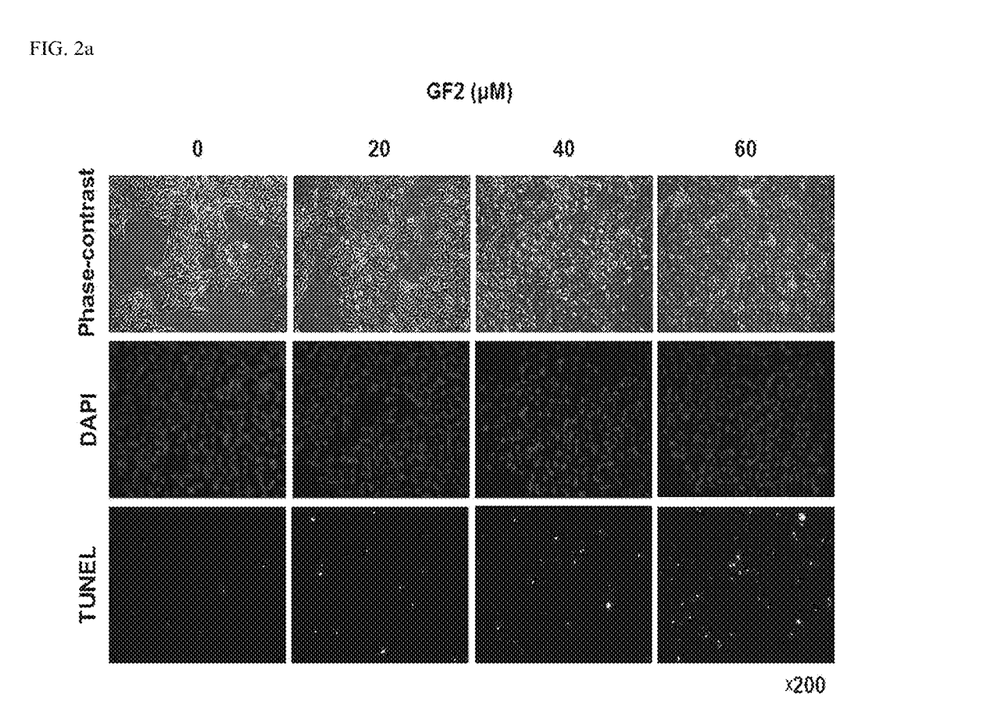
FIG. 2a is an image showing the cell-killing effect of ginsenoside F2 on human liver cancer cell line (Hep3B) through a phase contrast microscope and a fluorescence microscope.
Figure 2B:
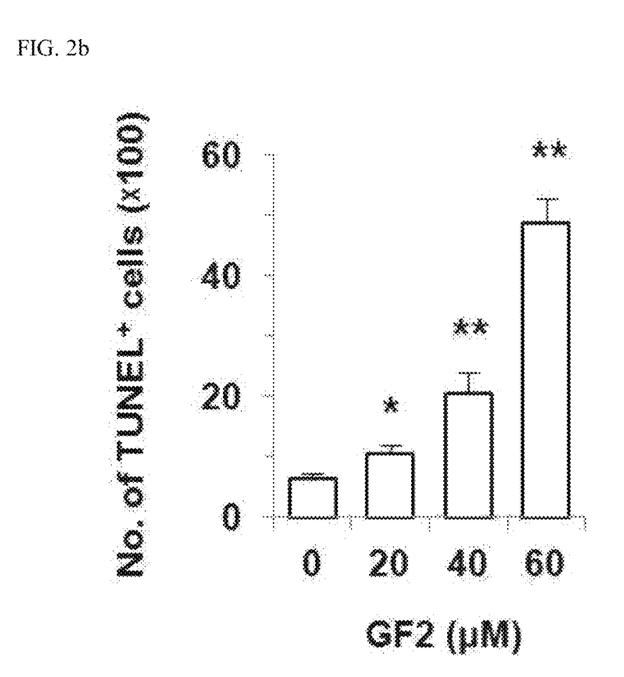
FIG. 2b is a graph showing the amount of human liver cancer cell line, in which cell death was induced by ginsenoside F2, through fluorescence.
Figure 3:
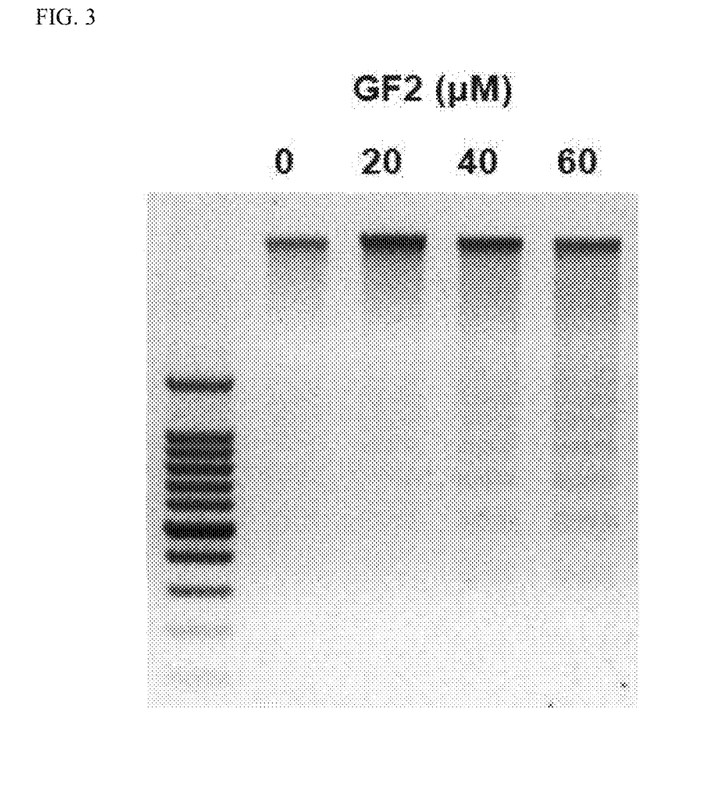
FIG. 3 is a graph showing an increase in fragmented DNA upon treatment with ginsenoside F2 on mouse liver cancer cell line (Hepa1-6).

In one embodiment of the present invention, when the ginsenoside F2 was treated to the human liver cancer cell line (Hep3B), it was confirmed that the survival rate of the liver cancer cell line was reduced in a concentration-dependent manner of ginsenoside F2 (FIGS. 1a, 2a, and 2b). Further, when the ginsenoside F2 was treated to the mouse liver cancer cell line (Hepa1-6), it was confirmed that the survival rate of the liver cancer cell line was reduced in a concentration-dependent manner of ginsenoside F2 (FIGS. 1b and 3). However, when the ginsenoside F2 was treated to normal hepatocytes, it was confirmed that it had no effect on the survival rate of the normal hepatocytes (FIG. 1c).

Accordingly, it was found that the pharmaceutical composition containing ginsenoside F2 as an active ingredient shows a specific cell-killing effect on liver cancer cells only, but does not have an effect on the normal cells, and thus can be used as a preventive or therapeutic agent for liver cancer without causing side effects.

In the present invention, the pharmaceutical composition may reduce the expression of alanine aminotransferase (ALT) or aspartate aminotransferase (AST).

As used herein, the term "alanine aminotransferase (ALT)" is an enzyme found in hepatocytes which forms glutamic acid by transferring an amino group of alanine to 2-oxoglutaric acid, and is used interchangeably with serum glutamic pyruvate transaminase (SGPT) or alanine aminotransferase (ALAT).

Since the alanine aminotransferase is released to serum when the hepatocytes are damaged, it can be used as an index for determining whether the hepatocytes are damaged, and specifically, it may be used in the present invention as an index for determining the damage of hepatocytes caused by liver cancer.

Further, as used herein, the term "aspartate aminotransferase (AST)" is an enzyme found in hepatocytes which forms glutamic acid by transferring an amino group of aspartic acid to 2-oxoglutaric acid, and is used interchangeably with serum glutamic oxaloacetic transaminase (SGOT) or aspartate aminotransferase (ASAT).

Since the aspartate aminotransferase is released to serum when the hepatocytes are damaged, it can be used with the alanine aminotransferase as an index for determining whether the hepatocytes are damaged, and specifically, it may be used in the present invention as an index for determining the damage of hepatocytes caused by liver cancer.

Figure 5A:
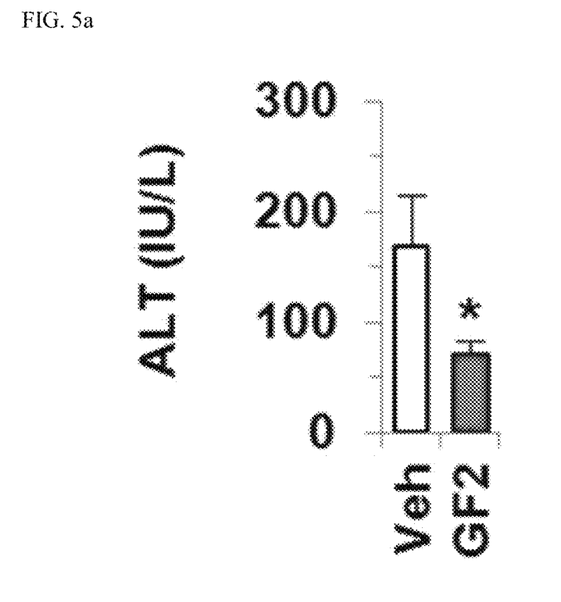
FIG. 5a is a graph showing the expression level of alanine aminotransferase (ALT) upon administration of ginsenoside F2 or vehicle to liver cancer-induced mice.
Figure 5B:
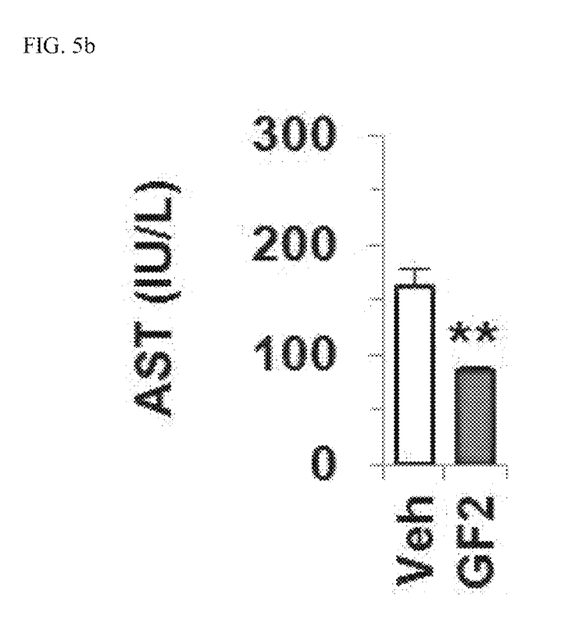
FIG. 5b is a graph showing the expression level of aspartate aminotransferase (AST) upon administration of ginsenoside F2 or vehicle to liver cancer-induced mice.

In one embodiment of the present invention, after treating the ginsenoside F2 to mice in which liver cancer was induced, the expression level of alanine aminotransferase (ALT) and aspartate aminotransferase (AST) in the serum of blood collected from the abdominal aorta of the mice was measured, and as a result, it was confirmed that the expression level of the proteins was reduced in the ginsenoside F2-treated group compared to the control group (FIGS. 5a and 5b).

Accordingly, it was found that the pharmaceutical composition containing ginsenoside F2 as an active ingredient shows an effect of preserving the liver function.

In the present invention, the pharmaceutical composition may increase the number of immune cells.

As used herein, the term "immune cell" generically refers to a cell that produces an antibody, and the immune cell may be at least one selected from the group including CD8 T cells, natural killer T cells, and macrophages, but is not limited thereto.

In one embodiment of the present invention, after treating the ginsenoside F2 to mice in which liver cancer was induced, followed by isolating the immune cells from the mouse liver, the cells were analyzed using various cell-specific markers, and as a result, it was confirmed that the number of CD8T cells, natural killer T cells, and macrophages was increased in the ginsenoside F2-treated group compared to the vesicle-treated group. (FIG. 6b).

Therefore, it was found that the pharmaceutical composition containing ginsenoside F2 as an active ingredient can inhibit the formation of liver cancer by increasing the number of the immune cells near the liver cancer tissues.

The pharmaceutical composition may include a pharmaceutically acceptable carrier. The term "pharmaceutically acceptable carrier" may refer to a carrier, excipient, or diluent which does not disturb the biological activity and properties of a compound being injected, without irritating an organism, and specifically, it may be a non-naturally occurring carrier. The type of carrier which can be used in the present invention is not specifically limited, but any carrier may be used as long as they are commonly used in the art and are pharmaceutically acceptable. Non-specific examples of the carrier include saline water, sterile water, Ringer's solution, buffered saline, albumin injection solution, dextrose solution, maltodextrin solution, glycerol, ethanol, etc. They can be used alone or in combination of two or more.

The pharmaceutical composition including the pharmaceutically acceptable carrier may be of various forms such as oral or parenteral forms. When formulated, it may be prepared using a diluting agent or an excipient, such as commonly-used fillers, weighting agents, bonding agents, wetting agents, disintegrating agents, and surfactants.

Specifically, the solid formulations for oral administration include tablets, pills, powders, granules, and capsules, etc., and such solid formulations may be prepared by mixing the compound with at least one excipient, for example, starch, calcium carbonate, sucrose, lactose, gelatin and the like. Further, in addition to simple excipients, lubricants, such as magnesium stearate and talc, may also be used. Liquid formulations for oral administration include suspensions, solutions, emulsions, syrup, etc., and may include various excipients, for example, wetting agents, sweeteners, flavoring agents, preservatives, etc., in addition to water and liquid paraffin, which are frequently used simple diluents. The formulations for parenteral administration include sterile aqueous solutions, non-aqueous solvents, suspensions, emulsions, lyophilization formulations, and suppositories. Examples of the non-aqueous solvents and suspensions include propylene glycol, polyethylene glycol, vegetable oil such as olive oil, and injectable esters such as ethyl oleate, etc. Witepsol, Macrogol, Tween 61, cacao butter, laurinum, and glycero-gelatin, etc. may be used as the suppository base.

In addition, the pharmaceutical composition of the present invention may include a pharmaceutically acceptable effective amount of ginsenoside F2. As used herein, the term "pharmaceutically acceptable effective amount" refers to an amount sufficient to treat a disease at a reasonable benefit/risk ratio applicable to a medical treatment, and may be administered in an amount of generally 0.001 to 1000 mg/kg, specifically 0.05 to 200 mg/kg, more specifically 0.1 to 100 mg/kg once or multiple times a day. However, for the purposes of the present invention, the specific therapeutic effective amount for a particular patient may preferably vary depending on various factors including the type and extent of the reaction to be achieved, specific composition including whether other preparations are used occasionally, the age, weight, general health condition, sex and diet of the patient, time of administration, route of administration and secretion rate of the composition, treatment period, drugs used along with or concurrently-used with the specific composition, and similar factors well known in the medical field.

The pharmaceutical composition of the present invention may be used as a therapeutic agent for liver cancer, an adjuvant additive capable of improving the efficacy of an anti-cancer agent, an auxiliary therapeutic agent (for example, anticancer auxiliary agent) capable of enhancing the therapeutic efficacy, etc.

In another aspect of the present invention, there is provided a food composition for preventing or improving liver cancer containing ginsenoside F2 as an active ingredient.

As used herein, the terms "ginsenoside F2" and "prevention" are the same as described above.

As used herein, the term "improvement" may refer to any action by which the parameters associated with conditions under treatment, for example, the degree of symptoms are lessened.

As used herein, the term "food" may include meat, sausages, bread, chocolates, candies, snacks, chips, pizza, ramen noodles, other noodles, gums, dairy products including ice cream, various kinds of soups, beverages, tea, drinks, alcoholic beverages, vitamin complexes, health functional food, and health food, and may include all food of common meaning.

The health functional food, which is referred to by the same term as "food for special health use" (FoSHU), refers to food having high medicinal and medical effects which have been processed such that the biological control functions can be efficiently exhibited in addition to the supply of nutrition. Herein, the term "functional" refers to obtaining a beneficial effect for health use such as control of nutrients or physiological actions with respect to the structure and functions of the human body. The food of the present invention may be prepared by a method commonly used in the art, and may be prepared by adding raw materials and ingredients that are commonly added in the art during the production. In addition, the food may be prepared, without limitations, as long as they are formulations of the food or formulations acceptable as food. The food composition of the present invention may be prepared in various formulations, and unlike common drugs, it has advantages of being free from side effects that may occur when a drug is administered for a long period of time as it is prepared by using food as raw materials, and of being highly portable, and thus, the food of the present invention may be ingested as an auxiliary to enhance the immunity-enhancing effect.

The health food refers to food which bring about an active health-preserving or enhancing effect compared to the common food, and health supplement food refers to food to be ingested for the purpose of health supplementation. In some cases, the terms of health functional food, health food, and health supplement food are used interchangeably.

Specifically, the health functional food is food prepared by adding ginsenoside F2 to a food material such as beverage, tea, spice, gum, chips, etc., or by encapsulation, powdering, or suspension, and brings about a specific effect to health for when consumed. However, unlike common drugs, it has advantages of being free from side effects that may occur when a drug is administered for a long period of time as it is prepared by using food as raw materials.

Since it is possible to routinely ingest the food composition of the present invention, it may be very useful as a high-improving effect on liver cancer may be expected.

The composition may further include a physiologically acceptable carrier, and the type of carrier is not particularly limited and any carrier commonly used in the art may be used.

Further, the composition may include additional ingredients which are commonly used in food compositions to improve odor, taste, vision, etc. For example, it may include vitamins A, C, D, E, B1, B2, B6, B12, niacin, biotin, folate, panthotenic acid, etc. Furthermore, it may include minerals such as zinc (Zn), iron (Fe), calcium (Ca), chromium (Cr), magnesium (Mg), manganese (Mn), copper (Cu), etc. In addition, it may include amino acids such as lysine, tryptophan, cysteine, valine, etc.

Moreover, the composition may include food additives such as preservatives (potassium sorbate, sodium benzoate, salicylic acid, sodium dehydroacetate, etc.), disinfectants (bleaching powder and high-grade bleaching powder, sodium hypochlorite, etc.), antioxidants (butylhydroxyanisole (BHA), butylhydroxytoluene (BHT), etc.), coloring agents (tar color, etc.), coloring fixing agents (sodium nitrite etc.), bleaching agents (sodium sulfite), seasoning (sodium glutamate (MSG), etc.), sweeteners (dulcin, cyclamate, sodium saccharin, etc.), flavoring agents (vanillin, lactones, etc.), swelling agents (alum, potassium hydrogen D-tartrate), reinforcing agents, emulsifying agents, thickener (thickening agents), coating agents, gum bases, foam inhibitors, solvents, enhancers, etc. These additives may be selected and used in an appropriate amount according to the type of food.

The ginsenoside F2 may be added alone or used together with other food or food ingredients, and may be appropriately used according to a conventional method. The mixing ratio of the active ingredients may be appropriately determined according to the purpose thereof (prevention, health, or therapeutic treatment). In general, during the production of food or beverage, the food composition of the present invention may be added in an amount of 50 parts by weight or less, specifically 20 parts by weight or less, based on the food or beverage. However, in case of a long-term ingestion for the purpose of health and hygiene, it may be added in an amount less than the range above, and since there is no problem in terms of safety, the active ingredients may be used in an amount exceeding the range above.

As an example of the food composition of the present invention, it may be used as a health beverage composition, and in this case, various flavoring agents or natural carbohydrates may be added as additional ingredients as in the case of common beverages. The above-mentioned natural carbohydrates may include monosaccharides such as glucose and fructose; disaccharides such as maltose and sucrose; polysaccharides such as dextrin and cyclodextrin; and sugar alcohols such as xylitol, sorbitol, erythritol, etc. Sweeteners may include natural sweeteners such as thaumatin and stevia extract; and synthetic sweeteners such as saccharin, aspartame, etc. The ratio of the natural carbohydrate is generally about 0.01 to 0.04 g, specifically about 0.02 to 0.03 g per 100 mL of the composition of the present invention.

In addition to the above, the health beverage composition may contain various nutritional supplements, vitamins, electrolytes, flavoring agents, coloring agents, pectic acid, salts of pectic acid, alginic acid, salts of alginic acid, organic acids, protective colloid thickening agents, pH adjusters, stabilizers, preservatives, glycerin, alcohol, or carbonating agents, etc. Alternatively, it may contain a flesh for the production of natural fruit juices, fruit juice drinks or vegetable drinks. These ingredients may be used independently or in combination. The ratio of such additives is not critical, but is generally selected in the range of 0.01 to 0.1 parts by weight based on 100 parts by weight of the composition of the present invention.

The food composition of the present invention may be contained in various weight percentages as long as it can exhibit a preventing or improving effect on liver cancer. Specifically, it may contain the ginsenoside F2 in an amount of 0.00001 to 100% by weight or 0.01 to 80% by weight based on the total weight of the food composition.

In still another aspect of the present invention, there is provided a method for preventing or treating liver cancer, comprising administering a composition containing ginsenoside F2 to a subject.

As used herein, the term "ginsenoside F2" is the same as described above

As used herein, the term "administration" refers to introduction of the composition of the present invention into a subject by a certain suitable method. The composition may be administered via any of the common routes, as long as it can reach a desired tissue. The route of administration may include intraperitoneal, intravenous, intramuscular, subcutaneous, intradermal, oral, topical, or intranasal administration, but is not limited thereto.

As used herein, the term "subject" refers to all animals such as rats, mice, livestock, etc. including human who require or may possibly require the prevention or treatment of liver cancer. Specifically, it may be a mammal including human.

The composition may be administered in a pharmaceutically effective amount.

The "pharmaceutically effective amount" refers to an amount sufficient to treat a disease at a reasonable benefit/risk ratio applicable to a medical treatment. An effective dose level may be determined depending on various factors including the type, severity, age, and sex of the subject, drug activity, drug sensitivity, time of administration, route of administration, excretion ratio, treatment period, and concurrently-used drugs, and other factors well known in the medical field. For example, the composition containing ginsenoside F2 may be administered at a daily dose of 0.0001 to 1000 mg/kg, specifically 0.001 to 100 mg/kg.

The composition may be administered daily or intermittently, and the daily administration frequency may be administered once, or in two or three divided doses. Further, the composition may be used alone or in combination with other drug therapies for the prevention and treatment of liver cancer. It is important to use the composition in the minimum possible amount sufficient to obtain the greatest therapeutic effect without side effects, considering all the factors, and such amount may be easily determined by one skilled in the art.

Advantageous Effects

The composition according to the present invention kills liver cancer cells, specifically inhibits the formation of liver cancer, and reduces the expression of alanine aminotransferase (ALT) or aspartate aminotransferase (AST), without affecting the normal hepatocytes, and thus can be usefully used as a therapeutic agent for liver cancer.

DESCRIPTION OF DRAWINGS

The unit of 1×10³/g refers to the number of cells present per liver tissue weight (g). The % refers to the ratio of the relevant number of cells among the number of immune cells isolated from liver tissue.

BEST MODE

Hereinafter, the composition and effects of the present invention will be described in detail by way of Examples. However, the Examples are for illustrative purposes only, and the scope of the invention is not intended to be limited by these Examples.

Example 1: Preparation of Ginsenoside F2

The method for preparing ginsenoside F2 is as follows.

Specifically, leaves and roots of ginseng including Korean ginseng, American ginseng, and Japanese ginseng were extracted twice by adding 20-fold volume of 80% alcohol and dried to obtain a crude saponin. The crude saponin was dissolved again in water, adsorbed on a HP-20 resin, and then washed with 100% water to remove sugar. After removing the sugar, ginsenosides Re and Rg1, which belong to the protopanaxatriol group, were preferentially removed by primary washing with 40% alcohol. Subsequently, after washing with 80% alcohol and drying, the eluted ginsenosides Rb1, Rb2, Rc, and Rd, which belong to the protopanaxadiol group, were obtained. By using the mixture of protopanaxadiol ginsenosides as a substrate, more than 70% of ginsenoside F2 was obtained according to the method disclosed in Korean Patent Publication No. 2013-0134930. The ginsenoside F2 was adsorbed by utilizing an ODS resin, and then a fraction of ginsenoside F2 having a high purity of 95% or higher was obtained by continuously flowing alcohol at a concentration appropriate for obtaining ginsenoside F2 in a concentration gradient.

Example 2: Cancer Cell-Killing Effect of Ginsenoside F2

Example 2-1: Comparison of Cell-Killing Effects on Human Liver Cancer Cell Line, Mouse Liver Cancer Cell Line, and Normal Hepatocytes The ginsenoside F2 prepared in Example 1 was treated to Hep3B cells, a human liver cancer cell line, Hepa1-6 cells, a mouse liver cancer cell line, and mouse normal hepatocytes at various concentrations (10 to 60 μM). After 24 hours, the survival rate of the cells was measured using EZ-CYTOX (Daeil Lab Service, Korea), which is used to measure the cell survival rate, according to the experimental method provided by the manufacturer.

As a result of the measurement, it was confirmed that the survival rate of human liver cancer cell line (Hep3B) and mouse liver cancer cell line (Hepa1-6) was decreased depending on the concentration of ginsenoside F2 (FIGS. 1a to 1b), whereas almost no change was observed in the mouse normal hepatocytes (FIG. 1c).

Accordingly, the ginsenoside F2 exhibited cytotoxicity against the liver cancer cell lines and thus showed a cell-killing effect thereon, but it did not exhibit cytotoxicity against the normal cells, thereby confirming that the ginsenoside F2 exhibited the specific cell-killing effect on the liver cancer cells.

Example 2-2: Cell-Killing Effect on Human Liver Cell Line

The cell-killing effect of ginsenoside F2 on the human liver cell line (Hep3B) was confirmed using a phase contrast microscope and a fluorescence microscope.

Specifically, the ginsenoside F2 prepared in Example 1 was treated to the human liver cancer cell line (Hep3B) at various concentrations (10 to 60 μM), and after 24 hours, the state of the cells was observed under the phase contrast microscope. Further, the cells were stained using DAPI (4',6-diamidino-2-phenylindole, Vector laboratory, USA) and TUNEL (terminal deoxyribonucleotidyl transferase mediated dUTP nick end labeling, Roche life science, USA). The staining was carried out according to the method provided by the manufacturer, and the degree of staining was observed under the fluorescence microscope.

As a result of the observation with the phase contrast microscope, it was confirmed that a cell death of human liver cancer cell line (Hep3B) was induced by ginsenoside F2 (FIG. 2a). Further, when observed under the fluorescence microscope, it was confirmed that there was no difference in the number of cells stained to DAPI, but the number of cells stained to TUNEL increased depending on the concentration of ginsenoside F2 (FIGS. 2a and 2b).

Accordingly, it was confirmed once again that the ginsenoside F2 exhibited cytotoxicity against the liver cancer cell line, thereby showing the cell-killing effect.

Example 2-3: Cell-Killing Effect on Mouse Liver Cell Line

The cell-killing effect of ginsenoside F2 on the mouse liver cancer cell line (Hepa1-6) was confirmed by confirming the degree of DNA degradation.

Specifically, the ginsenoside F2 prepared in Example 1 was treated to the mouse liver cancer cell line (Hepa1-6) at various concentrations (10 to 60 p. 1\4). After 24 hours, the cells were harvested, and the genomic DNA was extracted using a genomic DNA extraction kit (iNtRON, USA) according to the experimental method provided by the manufacturer, and subsequently, a gel electrophoresis was carried out.

As a result, it was confirmed that the genomic DNA which had been fragmented by ginsenoside F2 appeared, and specifically that the fragmented genomic DNA increased with increasing concentration of ginsenoside F2 (FIG. 3).

Accordingly, it was confirmed once again that the ginsenoside F2 exhibited cytotoxicity against the liver cancer cell line, thereby showing the cell-killing effect.

Example 3: Inhibitory Effect of Ginsenoside F2 on Formation of Liver Cancer

Example 3-1: Preparation of Mice in which Liver Cancer Formation was Induced

Diethylnitrosamine (DEN), a hepatocarcinogen, was injected intraperitoneally into 14-day-old male mice at a concentration of 20 mg/kg to induce the formation of liver cancer. A vehicle (olive oil) or ginsenoside F2 (50 mg/kg) was treated three times a week from 20 weeks of age, and then 20 weeks later, the mice were sacrificed to confirm the inhibition of liver cancer formation.

Example 3-2: Inhibitory Effect of Ginsenoside F2 on Formation of Liver Cancer

The mice sacrificed in Example 3-1 above were cut open ventrally to remove the liver. Then, the size, number, and weight of the cancer tissues of the vehicle-treated group and the ginsenoside F2-treated group were compared.

As a result of the comparison, it was confirmed that the size of cancer tissues was significantly reduced and the number thereof was reduced more than twice in the ginsenoside F2-treated group compared to the vehicle-treated group (FIGS. 4a to 4c). In addition, although there was no difference in body weight of both treatment groups, it was confirmed that the weight of liver tissues was reduced in the ginsenoside F2-treated group compared to the vehicle-treated group (FIGS. 4d to 4f).

Accordingly, it was confirmed that the ginsenoside F2 exhibited the inhibitory effect on the formation and proliferation of liver cancer.

Example 3-3: The Preservation Effect of Ginsenoside F2 on Liver Function

Blood was collected from the abdominal aorta of the mice sacrificed in Example 3-1 above and centrifuged at 3,300 rpm for 10 minutes using a centrifuge, and then the serum was isolated only. Subsequently, the alanine aminotransferase (ALT), aspartate aminotransferase (AST) and triglyceride were measured by a VetTEST® (IDEXX, USA) according to the experimental method provided by the manufacturer using a kit provided by IDEXX Laboratories (USA).

As a result of the measurement, it was confirmed that ALT and AST values, which imply the damage of hepatocytes, were reduced in the ginsenoside F2-treated group compared to the vehicle-treated group (FIGS. 5a and 5b).

Accordingly, it was confirmed that the ginsenoside F2 inhibited the formation of liver cancer, and at the same time, exhibited the effect of preserving the liver function.

Example 3-4: Immune Cell-Increasing Effect of Ginsenoside F2

The mice sacrificed in Example 3-1 above were cut open ventrally to remove the liver, and then H&E (hematotoxic and eosin) staining was performed to observe the histological changes of the liver.

Figure 6A:
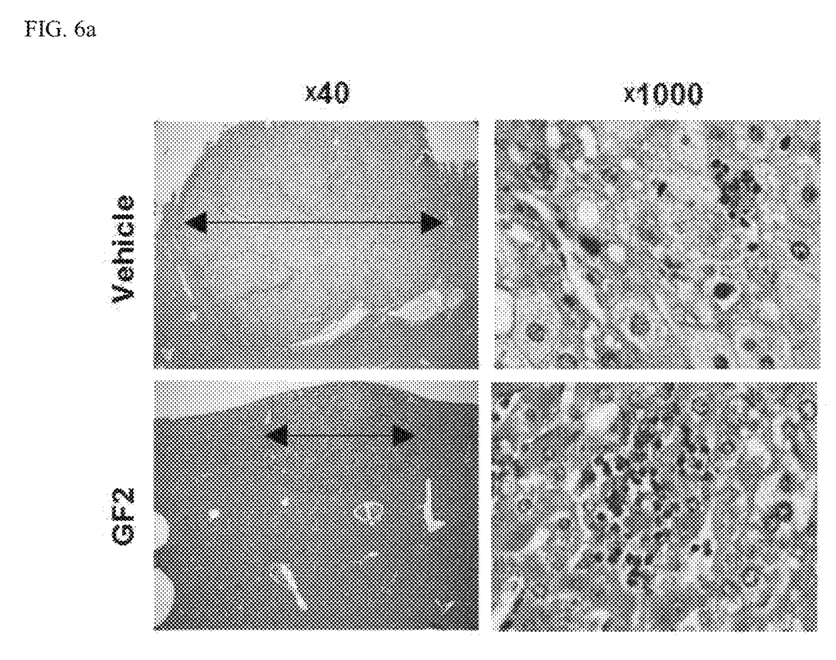
FIG. 6a is an image showing the inhibition of formation of liver cancer and increase in infiltration of immune cells upon administration of ginsenoside F2 or vehicle to liver cancer-induced mice.
Figure 6B:
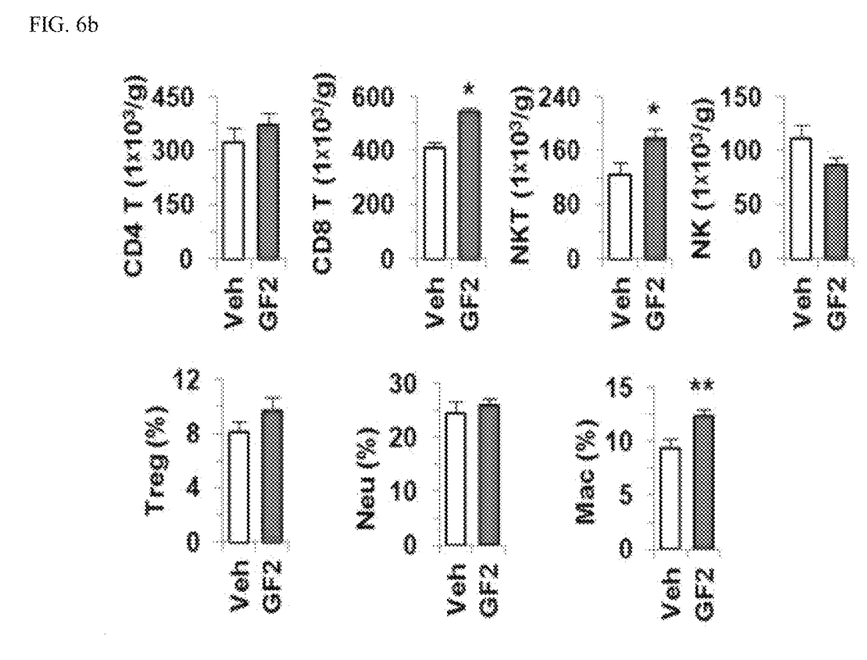
FIG. 6b is a graph showing the number of CD4 T cells, CD8 T cells, natural killer cells, natural killer T cells, regulatory T cells (Tregs), neutrophils (Neu), and macrophages (Mac), which are immune cells, upon administration of ginsenoside F2 or vehicle to liver cancer-induced mice.

As a result, it was confirmed in the ginsenoside F2-treated group that the formation of liver cancer was inhibited and the infiltration of immune cells was increased near the liver cancer tissues compared to the vehicle-treated group (FIG. 6a).

In order to specifically measure the activity of the immune cells, the immune cells were isolated from the removed liver, and the stained cells were analyzed via a flow cytometer (LSRII, BD bioscience) using the markers shown in Table 1.

TABLE 1

| Types of cells | Marker used |
|---|---|
| CD4 T cells | CD3e, CD4 |
| CD8 T cells | CD3e, CD8 |
| Natural killer cells, Natural killer T cells | CD3e, NK1.1 |
| Regulatory T cells (Treg) | CD4, CD25, Foxp3 |
| Neutrophils (Neu) | CD11b, Gr.1 |
| Macrophages (Mac) | CD11b, F4/80 |

As a result, it was confirmed that the ginsenoside F2-treated group showed an increase in the number of the CD8 T cells, natural killer T cells, and macrophages among the immune cells compared to the vehicle-treated group (FIG. 6b).

Accordingly, it was confirmed that the ginsenoside F2 exhibited the effect of increasing the number of the CD8 T cells, natural killer T cells, and macrophages near the liver cancer tissues which inhibit the proliferation of liver cancer.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents and other embodiments that may be included within the spirit and scope of the present invention as defined by the appended claims.

The invention claimed is:

1. A method for treating liver cancer, comprising a step of administering a pharmaceutically effective amount of an isolated ginsenoside F2 to a subject having liver cancer.

2. The method of claim 1, wherein the isolated ginsenoside F2 exhibits a specific cell-killing effect on liver cancer cells.

3. The method of claim 1, wherein the isolated ginsenoside F2 reduces the expression of alanine aminotransferase (ALT) or aspartate aminotransferase (AST).

4. The method of claim 1, wherein the isolated ginsenoside F2 increases the number of immune cells.

5. The method of claim 4, wherein the immune cell is at least one selected from the group consisting of CD8 T cells, natural killer T cells, and macrophages.

6. A method for improving liver cancer, comprising a step of administering a pharmaceutically effective amount of an isolated ginsenoside F2 to a subject having liver cancer.

* * * * *